United States Patent [19]
Steffan et al.

[11] Patent Number: 6,011,619
[45] Date of Patent: Jan. 4, 2000

[54] SEMICONDUCTOR WAFER OPTICAL SCANNING SYSTEM AND METHOD USING SWATH-AREA DEFECT LIMITATION

[75] Inventors: Paul J. Steffan, Elk Grove; Bryan Tracy, Oakland; Ming Chun Chen, Milpitas, all of Calif.

[73] Assignee: Advanced Micro Devices, Sunnyvale, Calif.

[21] Appl. No.: 08/987,736

[22] Filed: Dec. 9, 1997

[51] Int. Cl.$^7$ .................................................... G01N 21/88
[52] U.S. Cl. ............................................................ 356/237.3
[58] Field of Search ............................. 356/237.3, 237.4, 356/239.8

[56] References Cited

U.S. PATENT DOCUMENTS

| | | | |
|---|---|---|---|
| 4,449,818 | 5/1984 | Yamaguchi et al. | 356/237 |
| 5,331,396 | 7/1994 | Yakawa et al. | 356/237 |

*Primary Examiner*—Richard A. Rosenberger
*Attorney, Agent, or Firm*—LaRiviere, Grubman & Payne, LLP

[57] ABSTRACT

A semiconductor wafer optical scanning system and method for determining defects on a semiconductor wafer is disclosed. The method for determining wafer defects is based on maximum allowable defects on a swath basis, rather than maximum allowable defects on a wafer basis. The method step include determining the scanned area of an individual swath that is based on a recipe set-up, consistent with the capability of the optical scanning equipment being used and the particular semiconductor wafer being tested for defects. The predetermined swath area is supplied and stored in the optical scanning system along with the maximum allowable defect density determined by the user. By using the predetermined maximum allowable defects for a swath as a limit, defect analysis may be performed on the entire wafer. The optical scanning system would stop acquiring defects for the current swath being analyzed whenever the defect limit is reached, or until the swath defect analysis has been completed. The optical scanning would proceed to the next swath determining its defect and continuing in such a manner until the wafer is completely scanned.

9 Claims, 2 Drawing Sheets

SEMICONDUCTOR WAFER OPTICAL SCANNING SYSTEM AND METHOD USING SWATH-AREA DEFECT LIMITATION

TECHNICAL FIELD

The present invention relates to defect analysis systems and techniques for optically scanning semiconductor wafers for manufacturing defects.

BACKGROUND OF THE INVENTION

In the evaluation of product wafers in a semiconductor production environment, a wafer scanning system is employed which uses a site to site comparison technique to determine if a difference exists between adjacent dice. If a difference exists, the location of that difference is noted and is marked as a defect. To perform this task the system scans a "swath" of a predetermined height across the surface of a wafer, from right to left and left to right, comparing like areas of adjacent dice to make a determination if defects are present. After completion of the current swath it indexes to the next swath area and scans it, and so on, until either the wafer is completed or a defect limit set at the wafer level is reached. Multiple swaths are necessary to scan the entire surface of the wafer. In the course of processing and evaluating wafers, such wafers exist which exhibit very high levels of defects in isolated portions of the wafer, see generally FIG. 3. In order to improve throughput, an arbitrary limit is placed on the system to account for, by example, no more than 5000 defects, since the throughput of the system is inversely proportional to the number of caught defects. If the 5000 limit is obtained the system stops scanning at the current location, (even if it is the first swath), rejects the wafer and begins scanning the next wafer in the queue. The difficulty with this system is information about the remainder of the wafer is lost, or at least never acquired, and vital areas of interest are left without data. Since the wafer containing the high quantity of defect is likely to be one which needs to be studied further for source and types of defects, a need is seen to exist for a wafer scanning system and technique which is not based on a defect limit set at the wafer level and which allows completion of the defect analysis of the wafer unit being tested.

Therefore, it is a primary object of the present invention to provide a wafer scanning system and technique which is not based on a defect limit set at the wafer level and which allows completion of the defect analysis of the wafer unit being tested.

BRIEF SUMMARY OF THE INVENTION

Accordingly, the primary object of the present invention is accomplished by providing a scanning system and method for determining wafer defects based on maximum allowable defects on a swath basis, rather than maximum allowable defects on a wafer basis. The method of the present invention comprises a step of determining the scanned area of an individual swath that is based on a recipe set-up, consistent with the capability of the optical scanning equipment being used and the particular semiconductor wafer being tested for defects. The predetermined swath area is supplied and stored in the optical scanning system along with the maximum allowable defect density determined by the user. By using the predetermined maximum allowable defects for a swath as a limit, defect analysis may be performed on the entire wafer. The optical scanning system would stop acquiring defects for the current swath being analyzed whenever the defect limit is reached, or until the swath defect analysis has been completed. However, instead of proceeding to the next wafer, the optical scanning would proceed to the next swath determining its defect and continuing in such a manner until the entire wafer is completely scanned. The benefits of the present invention include the following: (1) Complete wafer level information can be obtained without impact to throughput. (2) Nuisance cluster defects near the beginning of a wafer scan will not prevent full scan of the wafer. (3) Scan files containing defect information will be more complete, allowing for later analysis by other review tools. (4) The necessity of re-scanning wafers for incomplete data will be greatly reduced, speeding up the analysis process.

Other features of the present invention are disclosed or apparent in the section entitled: "DETAILED DESCRIPTION OF THE INVENTION"

BRIEF DESCRIPTION OF DRAWINGS

For fuller understanding of the present invention, reference is made to the accompanying drawing: In the drawings.

Figure 1:
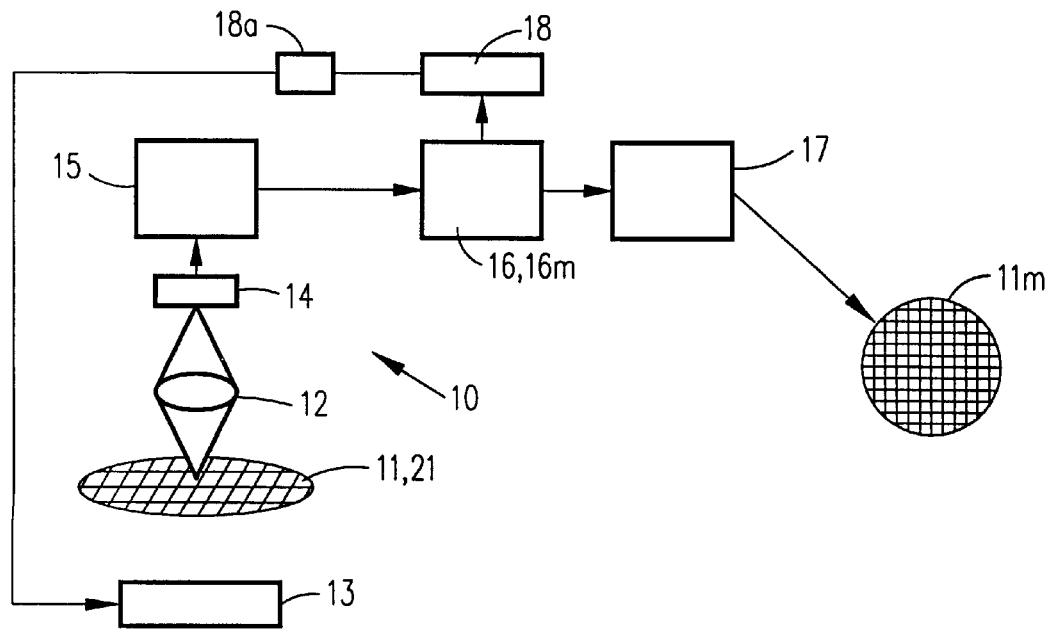
FIG. 1 shows a generalized diagram of a semiconductor wafer optical scanning system depicting wafer defect scanning operation control based on a per-swath defect limit in accordance with the present invention.

Reference numbers refer to the same or equivalent parts of the present invention throughout the several figures of the drawing.

DETAILED DESCRIPTION OF THE INVENTION

Figures 2, 3:
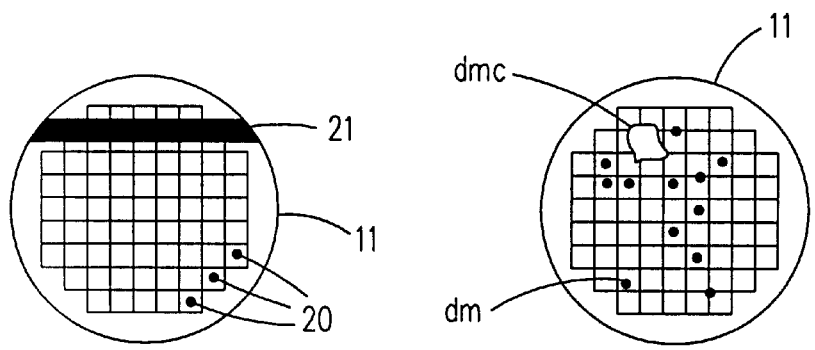
FIG. 2 shows a semiconductor wafer and a wafer dice portion delineating a swath area, as well as dice edges delineating start and end of swath area, in accordance with the present invention.
FIG. 3 shows a representative semiconductor wafer with manufacturing defect clusters and smaller defect regions which are the subject of the optical scan analysis.
Figures 4, 5:
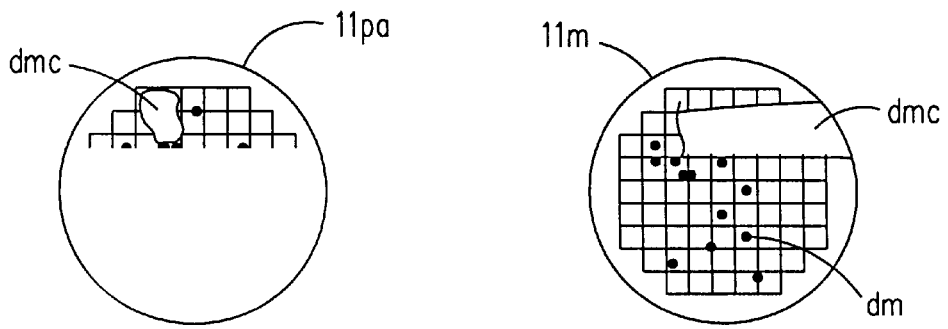
FIG. 4 shows a semiconductor wafer map that results from using prior art wafer scanning techniques based on defect limits set at the wafer level.
FIG. 5 shows a semiconductor wafer map that results from using wafer scanning techniques based on defect limits set at the swath level in accordance with the present invention.

Referring now to FIG. 1 where an optical scanning system 10 is shown in block diagram form. As illustrated, optical scanning system 10 is configured for analyzing semiconductor wafers, generally depicted as wafer 11, which are appropriately positioned and aligned at a mechanical wafer staging area 13. FIG. 3 shows a representative semiconductor wafer 11 with manufacturing defect clusters dmc and smaller defect regions dm which are the subject of the optical scan analysis. Optical scanning system 10 comprises a plurality of optical scanning components, such as system optics 12, image sensors 14, image acquisition station 15, image computer 16 and post processing station 17, which comprise commercially available system components. As discussed previously, the prior art optical scanning systems are controlled for fast throughput of wafers and as a result leave critical manufacturing defect information as a result of not completing the defect analysis because the wafer defect limit has been reached. FIG. 4 shows a semiconductor wafer map 11pa that results from using prior art wafer scanning techniques based on defect limits set at the wafer level. The wafer map 11pa is incomplete as a result of stopping the scan operation due to having detected a cluster of manufacturing defects dmc that equaled the wafer defect limit at the wafer level. Optical scanning system 10 avoids the problem of incomplete analysis and includes a wafer scan control mechanism 18 and 18a that are coupled back to the wafer staging area, where a scan on a swath is being performed, and to computer 16. FIG. 2 shows a semiconductor wafer 11 and a wafer dice portion delineating a wafer swath area 21. Wafer 11 is circular, however the swath area's end and start edges are well defined rectangular die boundaries 20. Wafer scan mechanism 18 is electronically coupled to computer 16 comprising memory 16m for storing wafer swath defect limit information. Wafer scan control mechanism 18 comprises a comparator that compares the wafer swath limit against a tally of detected manufacturing defects being generated by computer 16 in accordance with any detected defects while scanning a wafer swath 21. If while scanning wafer swath 21 the tally of defects reaches the swath defect limit, or if the end-of-swath die is reached, then wafer scan control mechanism portion 18a causes the scanning operation at mechanical wafer staging area 13 to advance, either to a new swath portion 21 on a wafer 11 being analyzed, or to an un-analyzed wafer 11 being held in a queue. Throughout the scanning operation, defect data is being generated and stored in scan data files within computer 16. Concurrently, the defect information is being mapped at post processing 17 to generate a representative wafer defect map 11m. FIG. 5 shows a semiconductor wafer map 11m that results from using wafer scanning techniques based on defect limits set at the swath level in accordance with the present invention. As depicted in FIG. 5, wafer 11 has a significant number of manufacturing defects dmc and dmm, which although exceeded the swath defect limit, the wafer is completely scanned to show the defects on the rest of the wafer, or more importantly, show the defects surrounding the cluster dmc of manufacturing defects that equaled, and probably exceeded the swath defect limit.

Figure 6:
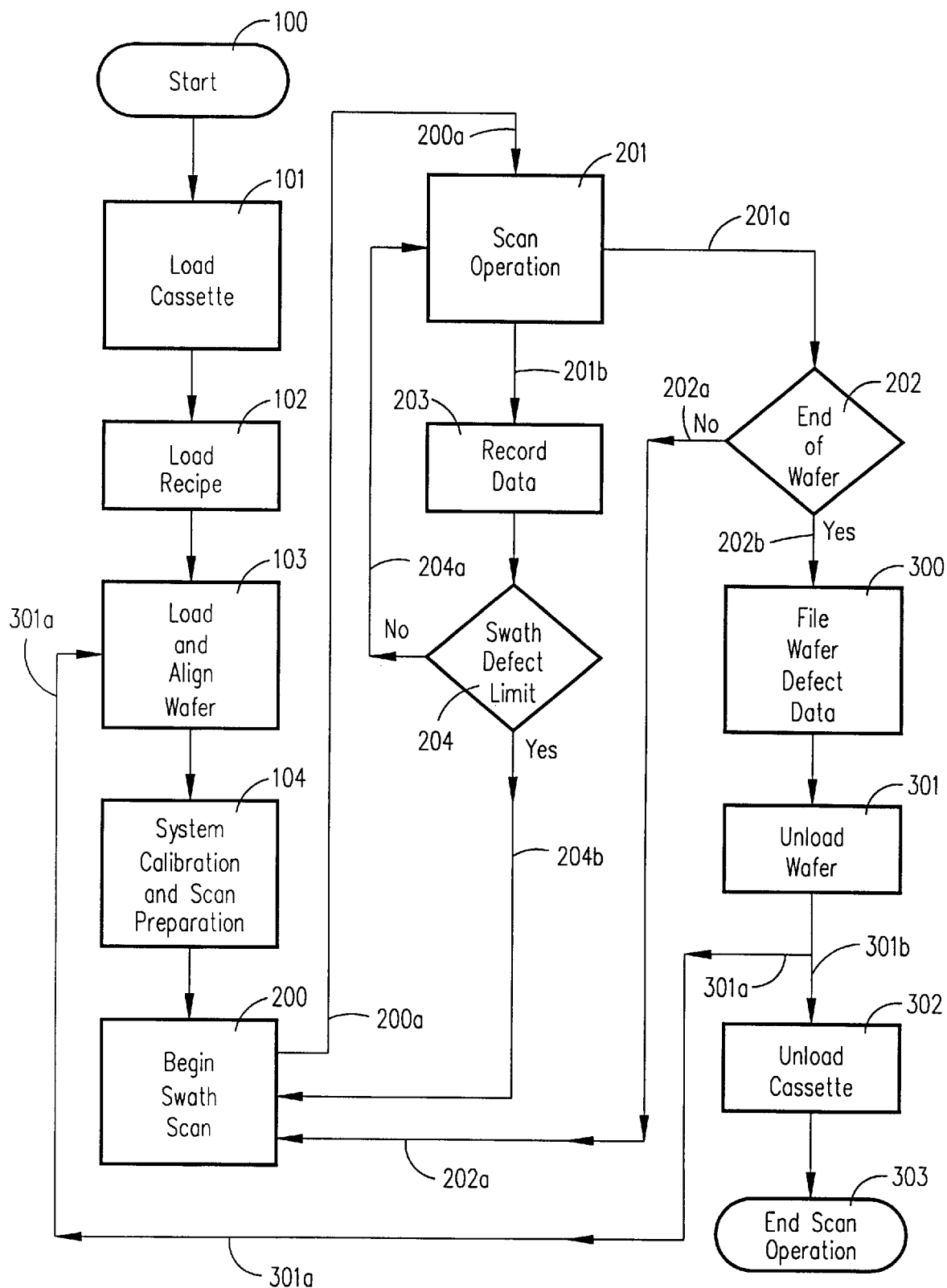
FIG. 6 is an optical scan process flow diagram for scanning semiconductor wafers for manufacturing defects based on swath defect limit, in accordance with the present invention.

FIG. 6 is an optical scan process flow diagram for scanning semiconductor wafers for manufacturing defects based on swath defect limit, in accordance with the present invention. The scanning process begins at step 100 and then proceeds to step 101 where a cassette containing wafer data is loaded to identify the batch of wafers being analyzed. Step 102 pertaining to loading a recipe is particularly important because the swath area definition for a wafer 11 is contained in the recipe. Step 103 pertains to loading the wafers and aligning them for beginning the scan operation. Once the wafers are ready, at the wafer staging station 13, a brief calibration and scan preparation step 104 is conducted. For example, the optics 12 are set at the beginning of a swath area 21 to begin the swath scan operation step 200. The scan operation 200 begins and the scan process flows according to process flow line 200a where the scan operation step 201 is a primary scanning step for control of scanning the wafer swaths. At operation step 201, the defects and end-of-swath (EOS) state are determined. If the EOS is reached the swath defect limit has not been reached. If a defect is determined, then a query is also made as to whether the end-of-swath (EOS) has been reached. If the EOS has been reached then line 201a is followed, otherwise line 201b is followed to record the defect information at step 203 and to further inquire at process step 204 as to whether the swath defect limit has been reached. If the swath defect limit has not been reached the line 204a is followed back to the scan operation 201 to continue on the same swath area searching for more defects. If the swath defect limit has been reach at step 204 then line 204b is followed to step 200 to begin scanning another swath and iteratively proceeding through step 201 following line 200a. If the EOS has been reached the query at step 202 establishes whether you are at the end of the wafer scan, If the scanning process is not complete on all the wafer swaths, then line 202a is followed back to step 200 to begin scanning another swath and proceeding through step 201 following line 200a. If the end of wafer has been reached at step 202, then line 202b is followed to step 300 where the wafer defect data is recorded before proceeding to step 301 where the analyzed wafer is unloaded, If the batch of wafers under analysis has been completed line 301b is followed where the cassette for that batch of wafers is unloaded at step 302 and the scan process is stop as indicated at step 303. Otherwise line 301a is followed back to step 103 where a new un-analyzed wafer is loaded to begin the scan operation on that particular wafer.

The present invention has been particularly shown and described with respect to a certain preferred embodiment and features thereof. However, it should be readily apparent to those of ordinary skill in the art that various changes and modifications in form, semiconductor material, material conductivity type i.e. N-type, or P-type, and detail may be made without departing from the spirit and scope of the inventions as set forth in the appended claims. The inventions illustratively disclosed herein may be practiced without any element which is not specifically disclosed herein.

What is claimed is:

1. A semiconductor wafer scanning method for determining defects on a semiconductor wafer, said method comprising the steps of:

(a) providing an optical scanning system for scanning semiconductor wafer defects;

(b) providing at least one semiconductor wafer to be analyzed for manufacturing defects;

(c) determining an area of a swath on said wafer to be scanned;

(d) programming said optical scanning system with a maximum quantity of allowable defects in a swath area;

(e) scanning and analyzing a swath area on said wafer for manufacturing defects;

(f) counting and tabulating manufacturing defects to determine a defect count;

(g) comparing said defect count against said maximum quantity of allowable defects in said swath area;

(h) completing said steps (e), (f) and (g) on all of said swath area if said defect count is less than said maximum quantity of allowable defects in said swath area, otherwise, stop performing said steps (e), (f) and (g) on said swath area if said defect count is equal to said maximum quantity of allowable defects in said swath area; and (i) repeating said steps (e), (f), (g) and (h) until said wafer is completely scanned regardless of whether said defect count in said step (f) is equal to, or less than, said maximum quantity of allowable defects in an individual swath area.

2. A semiconductor wafer scanning method as described in claim 1, wherein:

said step (a) includes providing said optical scanning system with scan file means for storing wafer manufacturing defect information; and said step (f) comprises storing wafer manufacturing defect information in said scan file means regardless of whether said defect count in said step (f) is equal to, or less than, said maximum quantity of allowable defects in an individual swath area.

3. A semiconductor wafer scanning method as described in claim 2, wherein:

said method further comprises a step of retrieving and analyzing stored manufacturing defect information from said scan file means about a semiconductor wafer whose defect count on a swath area equals said maximum quantity of allowable defects in an individual swath area.

4. A semiconductor wafer scanning method as described in claim 1, wherein:

said maximum quantity of allowable defects in an individual swath area is at least 5000 defects.

5. A semiconductor wafer scanning method as described in claim 1, wherein:

said step (b) comprises providing a plurality of semiconductor wafers to be analyzed for manufacturing defects; and said method further comprises a step of repeating said steps (e), (f), (g), (h) and (i) until said plurality of wafers are completely scanned regardless of whether said defect count in said step (f) is equal to, or less than, said maximum quantity of allowable defects in an individual swath area of a wafer being scanned.

6. An optical scanning method for determining manufacturing defects on a semiconductor wafer, said method comprising the steps of:

(a) programming an optical scanning system with a maximum quantity of allowable defects in a swath area of a semiconductor wafer, said optical scanning system having a scan file means for storing wafer manufacturing defect information;

(b) optically scanning and analyzing a swath area on a semiconductor wafer being analyzed for manufacturing defects;

(c) counting and tabulating manufacturing defects to determine a defect count;

(d) storing wafer manufacturing defect information in said scan file means for each manufacturing defect counted in said step (c);

(e) comparing said defect count against said maximum quantity of allowable defects in said swath area;

(f) completing said steps (b), (c) (d) and (e) on all of said swath area if said defect count is less than said maximum quantity of allowable defects in said swath area, otherwise, stopping execution of said steps (e), (f) and (g) on said swath area if said defect count is equal to said maximum quantity of allowable defects in said swath area;

(h) retaining said stored wafer manufacturing defect information regardless of whether said defect count in said step (c) is equal to, or less than, said maximum quantity of allowable defects in an individual swath area; and (i) repeating said steps (b), (c), (d) (f) and (g) until all swath areas of said wafer being analyzed are completely scanned regardless of whether said defect count in said step (c) is equal to, or less than, said maximum quantity of allowable defects in an individual swath area.

7. An optical scanning method for determining manufacturing defects on a semiconductor wafer as described in claim 6, wherein said method further comprises:

retrieving said retained wafer manufacturing defect information and conducting further wafer defect analysis.

8. An optical scanning method for determining manufacturing defects on a semiconductor wafer as described in claim 6, wherein:

said step of retrieving and analyzing said retained wafer manufacturing defect information comprises defect information about a semiconductor wafer whose defect count on a swath area equals said maximum quantity of allowable defects in an individual swath area.

9. An optical scanning system for determining manufacturing defects on a semiconductor wafer, said system comprising:

an optical scanning system adapted with mechanical, optical imaging and computer means for manipulating at least one semiconductor wafer for determining manufacturing defects;

a memory means member of said computer means, said memory means having a swath area defect limit stored within its memory elements, said swath area defect limit comprising a recipe for determining manufacturing defects in a swath portion of a semiconductor wafer undergoing defect analysis;

a first counter means member of said computer means for maintaining a manufacturing defect count on a per-swath basis;

a second counter means member of said computer means for maintaining a manufacturing defect count on a per-wafer basis; and a command instruction in said memory means for controlling said optical scanning to proceed to an end-of-swath location upon said first counter means obtaining a defect count that is equal to said swath area defect limit.

* * * * *